United States Patent [19]
Lundquist

[11] Patent Number: 5,681,276
[45] Date of Patent: Oct. 28, 1997

[54] MEDICAL PROBE DEVICE AND ELECTRODE ASSEMBLY FOR USE THEREWITH

[76] Inventor: Ingemar H. Lundquist, 17 Mile Dr. at 1154 The Dunes, Pebble Beach, Calif. 93953-1186

[21] Appl. No.: 424,162

[22] Filed: Apr. 19, 1995

[51] Int. Cl.$^6$ .................................................. A61B 17/39
[52] U.S. Cl. .................................................. 604/22
[58] Field of Search ...................... 604/164, 280, 604/19–22, 53; 601/2; 606/39, 32, 45, 47, 48; 607/96, 101, 102, 113, 115, 116, 138, 156

[56] References Cited

U.S. PATENT DOCUMENTS

| | | | |
|---|---|---|---|
| 4,565,200 | 1/1986 | Cosman | 128/642 |
| 4,950,267 | 8/1990 | Ishihara et al. | 608/12 |
| 5,370,675 | 12/1994 | Edwards et al. | 607/101 |

FOREIGN PATENT DOCUMENTS

| | | |
|---|---|---|
| 9210142 | 6/1992 | WIPO . |
| WO93/25136 | 12/1993 | WIPO . |
| WO94/20037 | 9/1994 | WIPO . |

*Primary Examiner*—Robert A. Hafer
*Assistant Examiner*—Manuel Mendez
*Attorney, Agent, or Firm*—Heller Ehrman White & McAuliffe

[57] ABSTRACT

A medical probe device for medical treatment of tissue of a prostate through a urethra defined by a urethral wall. The device includes a probe housing having proximal and distal extremities and a longitudinal axis. A handle is mounted on the proximal extremity of the probe housing for introducing the distal extremity of the probe housing into the urethra so that the distal extremity of the probe housing is in the vicinity of the prostate. The device has first and second guide tubes provided with lumens therein and having distal extremities. The first and second guide tubes extend distally of the probe housing and extend at an angle with respect to the longitudinal axis to form a space between the distal extremity of the probe housing and the distal extremities of the first and second guide tubes. A plate having a rounded distal portion is secured to the distal extremities of the first and second guide tubes. The plate has holes therein in communication with the lumens in the first and second guide tubes.

27 Claims, 10 Drawing Sheets

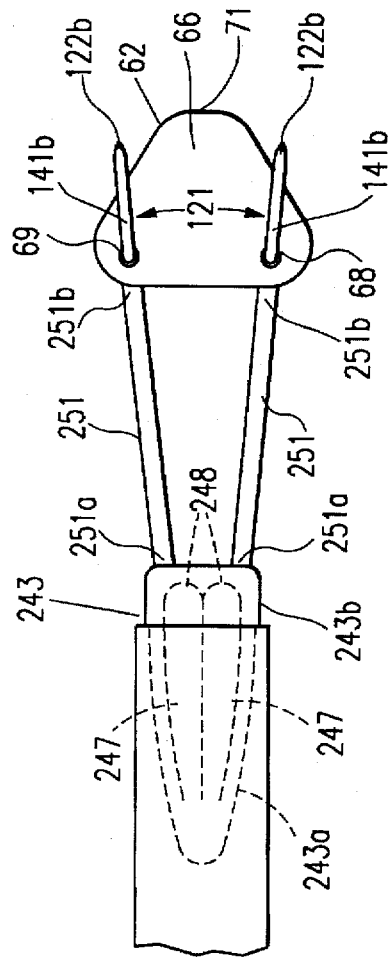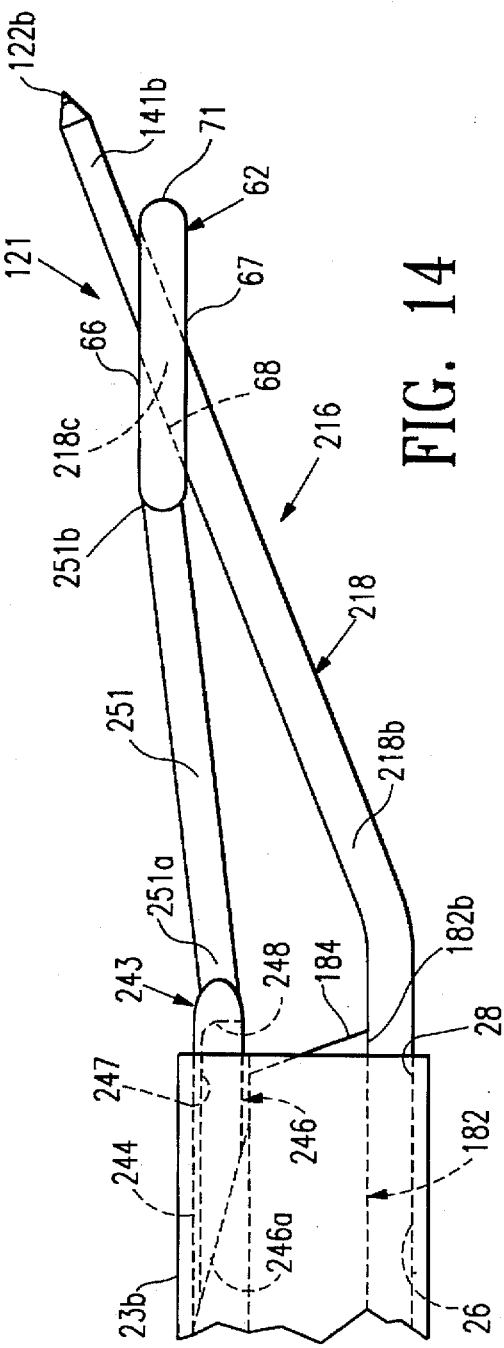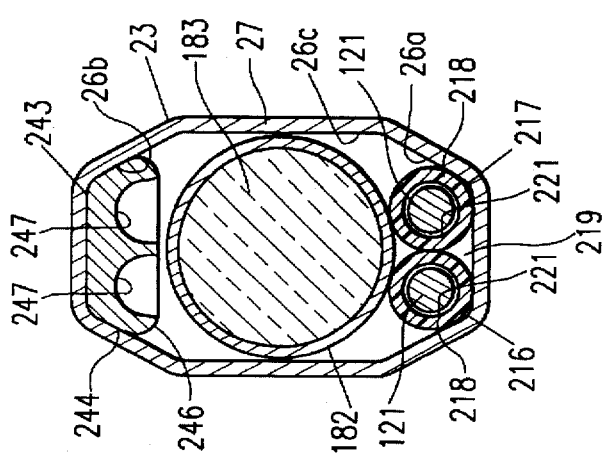

MEDICAL PROBE DEVICE AND ELECTRODE ASSEMBLY FOR USE THEREWITH

This invention pertains generally to medical probe devices and, more particularly, to transurethral medical probe devices having electrodes for ablating the tissue of the prostrate.

Medical probe devices such as transurethral needle ablation devices have heretofore been provided for treating the tissue of the prostate of human males. These devices include electrodes for penetrating the urethral wall so as to perform needle ablations within the prostate. Many of these devices are disposed of after a single use, thus increasing the cost of the procedure. There is, therefore, a need for a new and improved medical probe device which overcomes these disadvantages.

In general, it is an object of the present invention to provide a medical probe device which can be utilized for a transurethral needle ablation procedure in the prostate of a human male.

Another object of the invention is to provide a medical probe device of the above character which includes a bridge assembly which can be easily sterilized for reuse.

Another object of the invention is to provide a medical probe device of the above character which includes a removable stand alone electrode assembly which can be discarded after a single use.

Another object of the invention is to provide a medical probe device of the above character which includes a plurality of electrode assemblies having different sized electrodes to fit large, medium and small prostates.

Another object of the invention is to provide a medical probe device of the above character which can be used with a conventional rod lens scope.

Another object of the invention is to provide a medical probe device of the above character which can be alternatively used with a plurality of conventional rod lens scopes.

Another object of the invention is to provide a medical probe device of the above character which includes means for flushing the scope lens during the procedure.

Additional objects and features of the invention will appear from the following description from which the preferred embodiments are set forth in detail in conjunction with the accompanying drawings.

Figure 1:
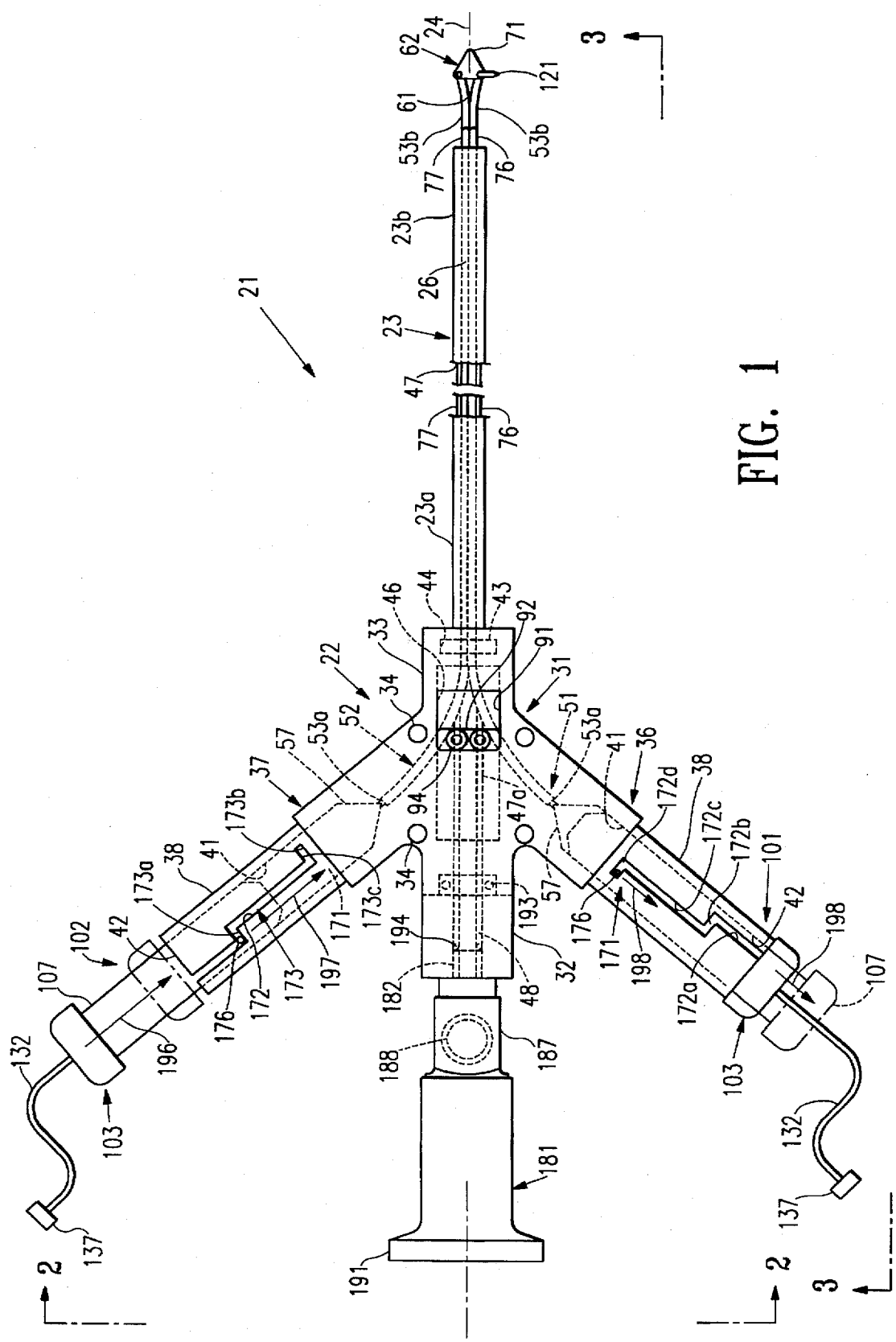
FIG. 1 is a bottom plan view of an embodiment of the medical probe device of the present invention.
Figure 8:
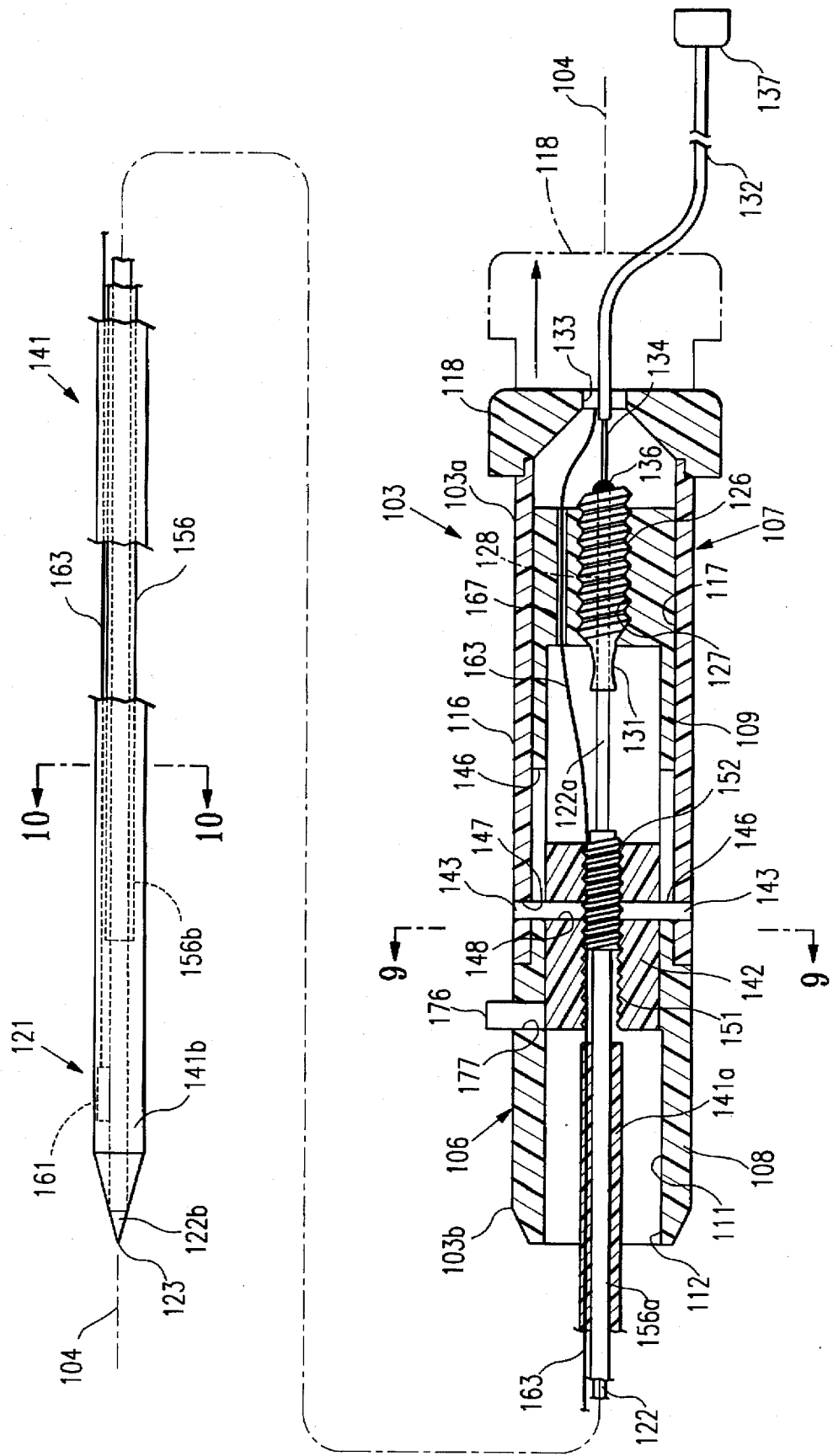

FIG. 8 a side elevational view of a portion of the medical probe device of FIG. 1.

Figure 9:
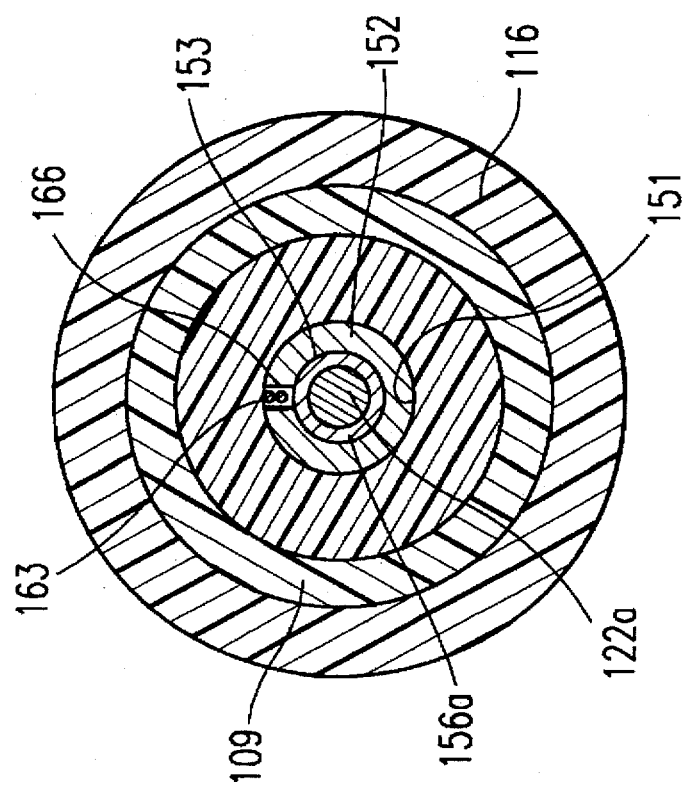

FIG. 9 is a cross-sectional view of the medical probe device of FIG. 1 taken along the line 9—9 of FIG. 8.

Figure 10:
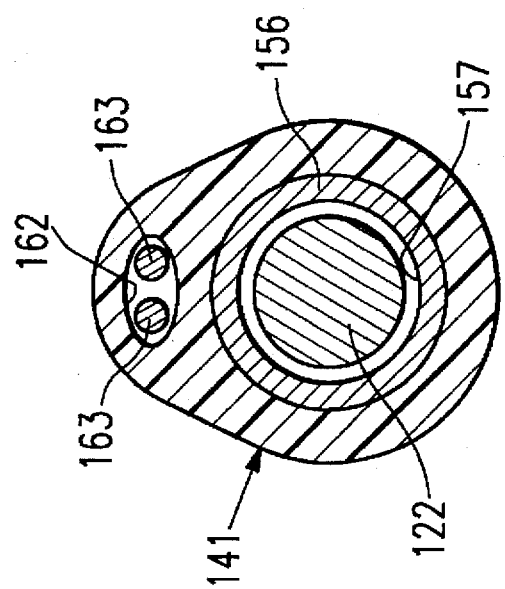

FIG. 10 is a cross-sectional view of the medical probe device of FIG. 1 taken along the line 10—10 of FIG. 8.

Figure 11:
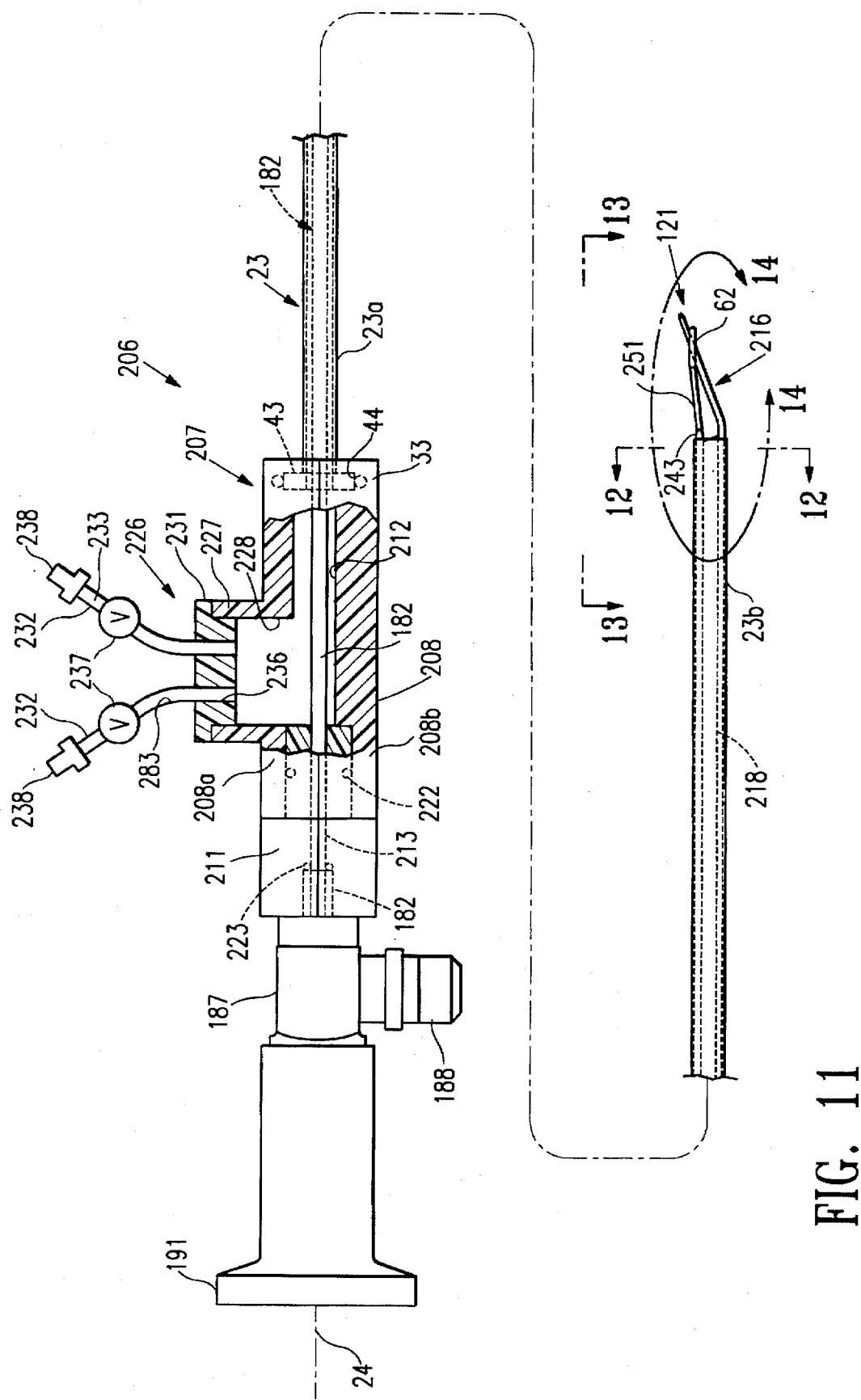

FIG. 11 is a side elevational view, partially cut away, of another embodiment of the medical probe device of the present invention.

FIG. 12 is a cross-sectional view of the medical probe device of FIG. 11 taken along the line 12—12 of FIG. 11.

FIG. 13 is an enlarged bottom plan view of the medical probe device of FIG. 11 taken along the line 13—13 of FIG. 11.

FIG. 14 is an enlarged view of the medical probe device of FIG. 11 taken along the line 14—14 of FIG. 11.

In general, a medical probe device is provided for medical treatment of tissue of a prostate through a urethra defined by a urethral wall. The device includes a probe housing having proximal and distal extremities and a longitudinal axis. Handle means is mounted on the proximal extremity of the probe housing for introducing the distal extremity of the probe housing into the urethra so that the distal extremity of the probe housing is in the vicinity of the prostate. The device has first and second guide tubes provided with lumens therein and having distal extremities. The first and second guide tubes extend distally of the probe housing and extend at an angle with respect to the longitudinal axis to form a space between the distal extremity of the probe housing and the distal extremities of the first and second guide tubes. A plate having a rounded distal portion is secured to the distal extremities of the first and second guide tubes. The plate has holes therein in communication with the lumens in the first and second guide tubes.

Figure 3:
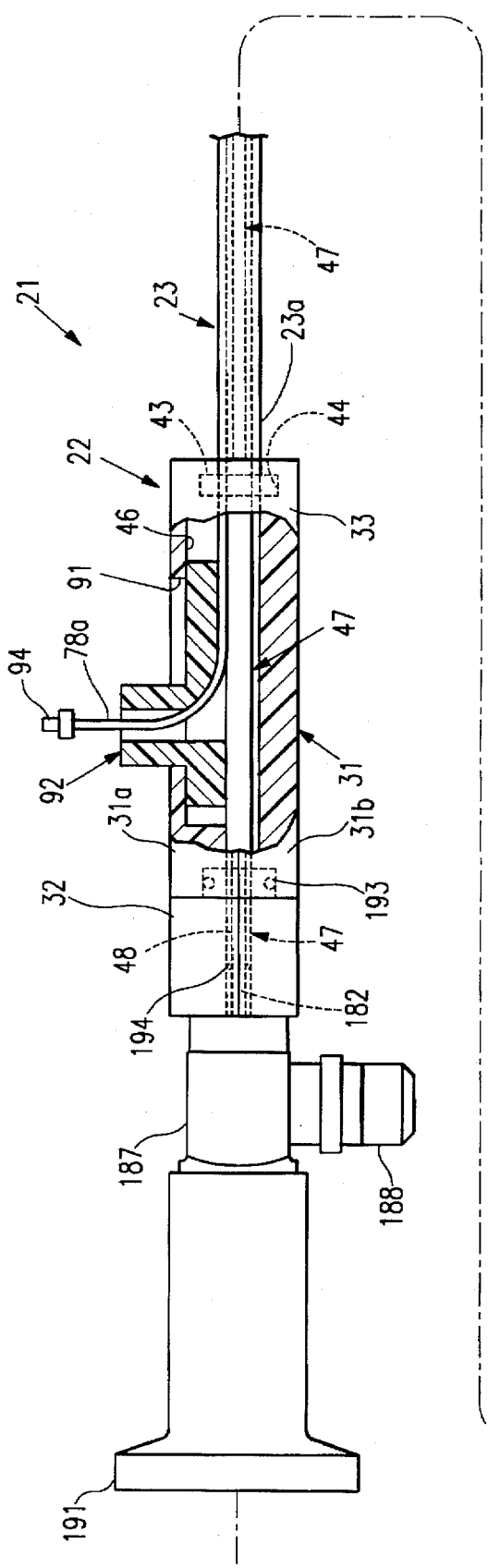
FIG. 3 is a side elevational view, partially cut away, of the medical probe device of FIG. 1 taken along the line 3—3 of FIG. 1.
Figure 3:
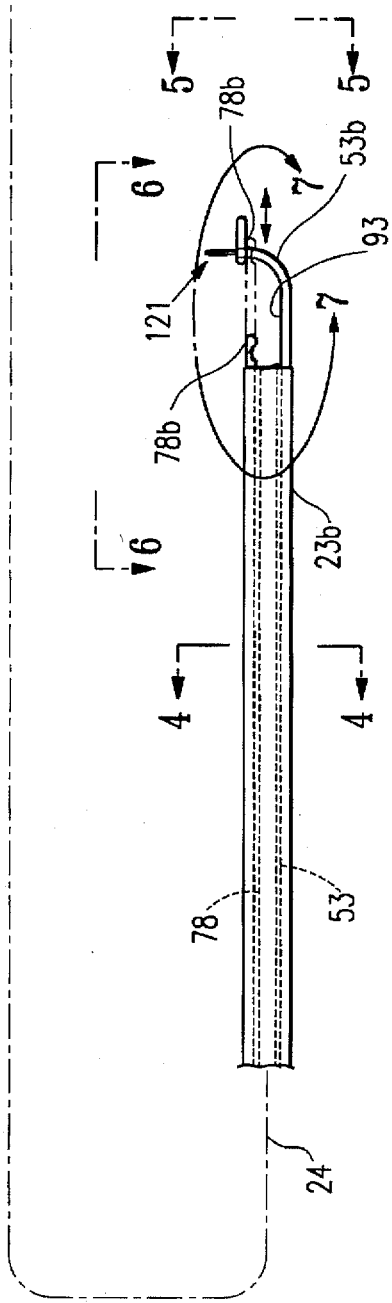
Figure 4:
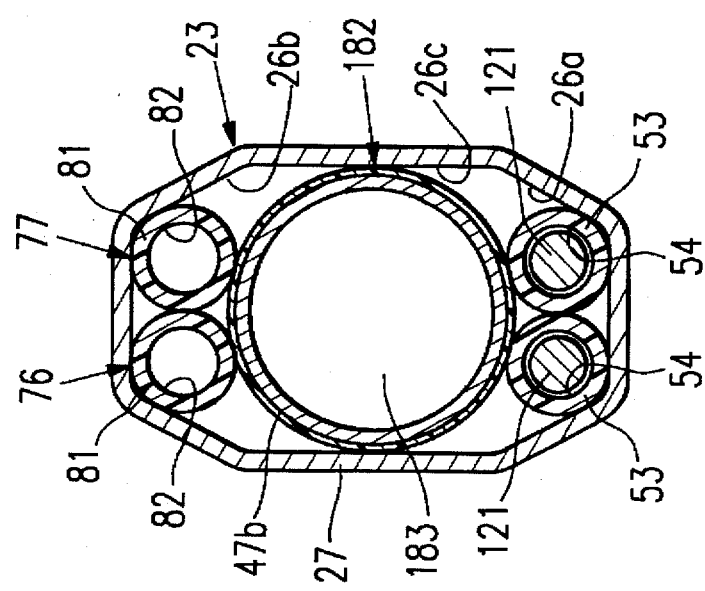
FIG. 4 is a cross-sectional view of the medical probe device of FIG. 1 taken along the line 4—4 of FIG. 3.

More in particular, the medical probe device of the present invention can be in the form of a transurethral needle ablation device 21 which includes a reusable bridge assembly 22. An elongate member or probe housing in the form of probe 23 is included in bridge assembly 22 and is made from stainless steel or any other suitable material. Probe 23 has a proximal extremity 23a and a distal extremity 23b (see FIGS. 1–4). Hollow cylindrical tube or probe 23 extends along a longitudinal axis 24 and has a length ranging from 9 to 10 inches and preferably approximately 9.5 inch. A bore 26 formed by probe wall 27 extends along longitudinal axis 24 between proximal extremity 23a and a distal opening 28 at the end of distal extremity 23b. Probe tube 23 is of a suitable transverse size as, for example, 23 French and is generally oblong-shaped in cross-section as shown in FIG. 4 so as to be provided with opposite first and second side or upper longitudinally-extending bore portions 26a and 26b and a central bore portion 26c extending longitudinally between portions 26a and 26b. In this regard, probe tube 23 has a large transverse dimension of approximately 0.3 inch and a small transverse dimension of approximately 0.2 inch.

Figure 2:
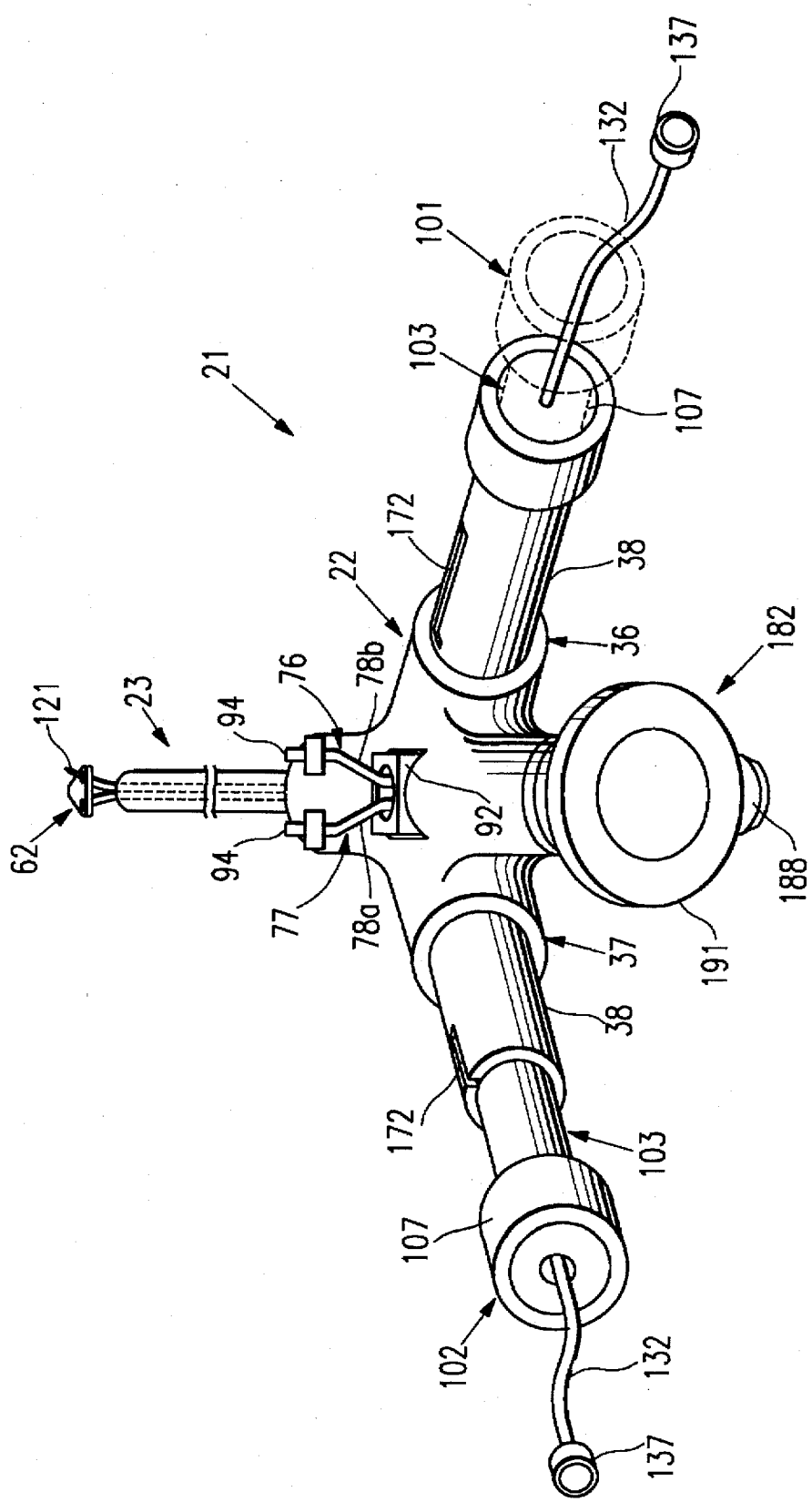
FIG. 2 is a rear isometric view of the medical probe device of FIG. 1 taken generally along the line 2—2 of FIG. 1.

Handle means is mounted on proximal extremity 23a of probe 23 and includes tricoupler or bridge 31 made from any suitable material such as polycarbonate. Bridge 31 is generally planar in conformation, as shown in FIGS. 2 and 3, and is aligned and generally centered on longitudinal axis 24. The bridge includes a proximal extremity in the form of removable adaptor 32 and a distal extremity in the form of neck 33 and has first and second halves 31a and 31b secured together by a plurality of four screws 34. Bridge 31 is further provided with oppositely aligned first and second coupling means or couplers 36 and 37 which each extend proximally from neck 33 at an angle of approximately 45° relative to longitudinal axis 24. Each coupler 36 and 37 includes a tubular sleeve 38 which is axially aligned along the respective coupler and defines a central bore 41 which is circular in cross-section and has a proximal opening 42. Means is carried by bridge 31 and probe 23 for securing the probe to the bridge and includes an annular flange 43 provided on proximal extremity 23a of probe 23 and a recess 44 formed in first and second halves 31a and 31b at neck 33. Recess 44 cooperatively receives flange 43 so that the probe extends distally from probe 33 along the longitudinal axis of device 21. The flange 43 can be press fit into annular recess 44 to permit disassembly of probe 23 and bridge 31, although flange 43 can be alternately fixedly secured and sealed within recess 44 by glue and be within the scope of the present invention. Bridge halves 31a and 31b are provided with respective cavities therein so as to form an internal chamber 46 within bridge 31 which is in communication with bore 26 in probe 23.

A scope guide tube 47 having proximal and distal extremities 47a and 47b extends along longitudinal axis 24 between the proximal and distal end portions of device 21 (see FIGS. 1 and 3–7). Tube 47 is made from stainless steel or any other suitable material and is secured within probe 23 by soldering or any other suitable means so as to extend along bore central portion 26c. Tube portion 47a extends proximally from annular flange 43 through internal chamber 46 into a longitudinally-extending central bore 48 provided in adapter 32.

At least one guide tube or member and, as shown in FIGS. 1 and 3, first and second guide members 51 and 52 are carried within bore 26 of probe 23. More specifically, guide members 51 and 52 each include a single tube 53 made from stainless steel or any other suitable material. Tube 53 has a proximal extremity 53a and a distal extremity 53b terminating at a distal end 53c. A lumen 54 extends between proximal and distal extremities 53a and 53b. Each tube 53 is circular in cross-section and has an external diameter of approximately 0.058 inch and an internal diameter of approximately 0.046 inch. The tubes 53 extend from respective couplers 36 or 37 through a curved path within internal chamber 46 so as to generally abut at annular flange 43 and extend through first side portion 26a of probe 23 in a side by side manner to the vicinity of probe distal extremity 23b. The proximal extremity 53a of each tube extends into the central bore 41 of the respective sleeve 38 so that lumen 54 of the tube 53 is in communication with bore 41 of the sleeve 38. Each of the couplers 36 and 37 includes a conical-shaped internal surface 57 at the distal end of its bore 41 so that the bore 41 funnels to an apex where it communicates with lumen 54. Tube distal extremities 53b are secured to distal extremity 23b of probe 23 by solder 56 which also serves to provide a fluid tight seal of probe first side bore portion 26a between tube distal extremities 53b and distal extremity 47b of scope guide tube 47 (see FIG. 5).

Figure 5:
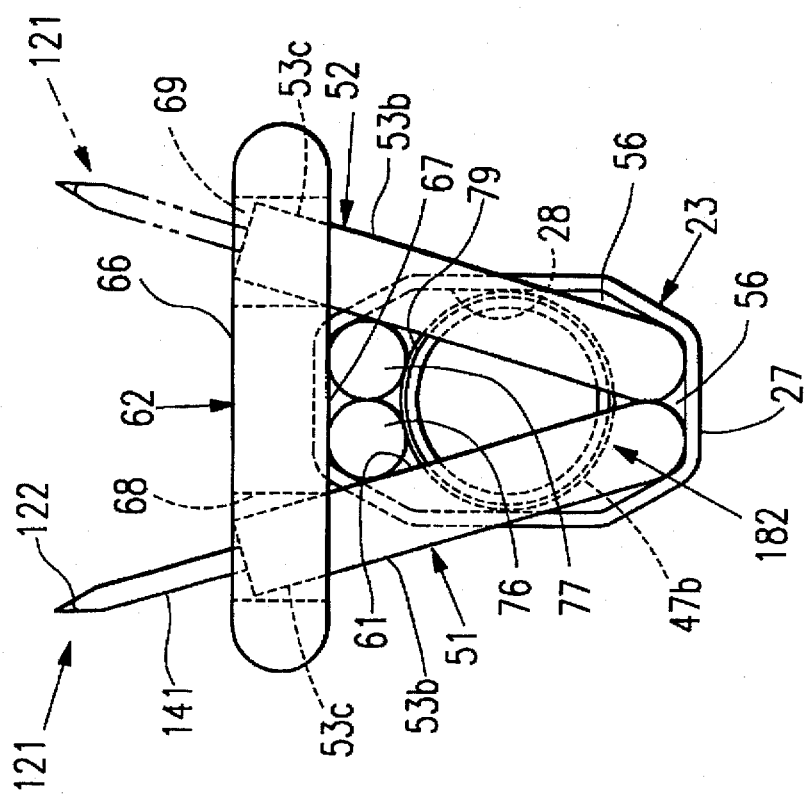
FIG. 5 is a front elevational view of the medical probe device of FIG. 1 taken along the line 5—5 of FIG. 3.
Figure 6:
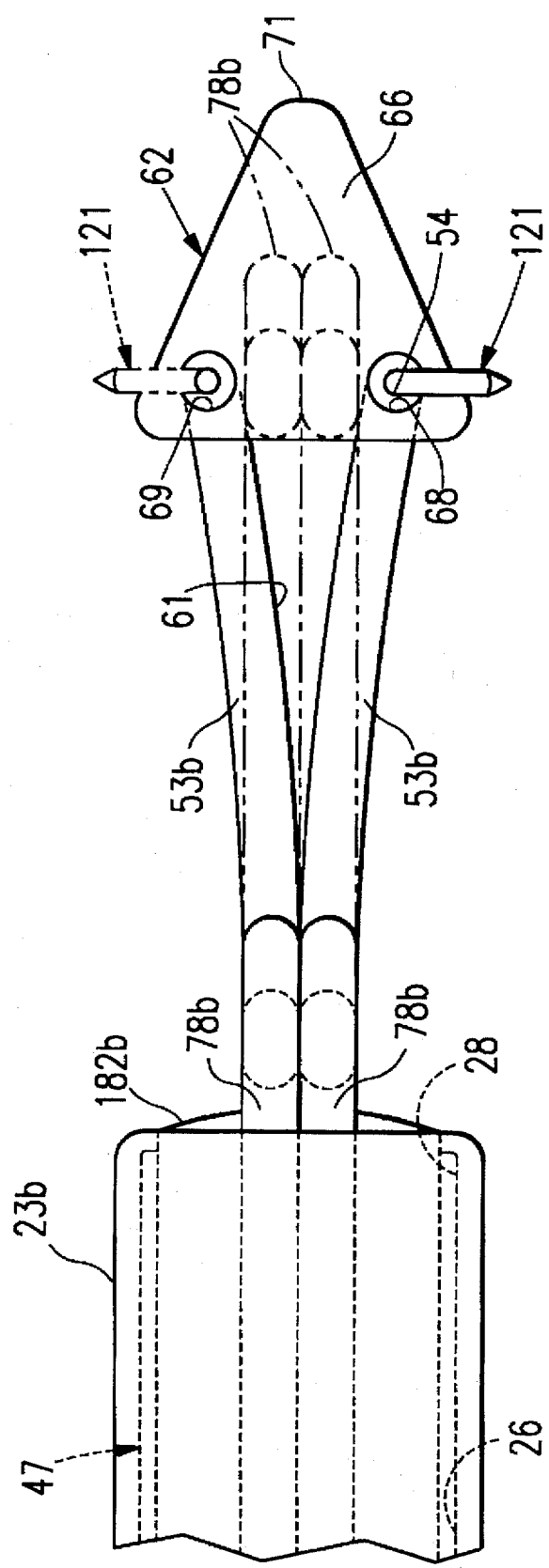
FIG. 6 is an enlarged bottom plan view of the medical probe device of FIG. 1 taken along the line 6—6 of FIG. 3.

Tube distal extremities 53b diverge with respect to longitudinal axis 24 as they extend distally out of probe bore 26 at an angle ranging from approximately 20° to 30° so as to form a space 61 therebetween (see FIGS. 5 and 6). The diverging tube distal extremities simultaneously curve alongside longitudinal axis 24 through an angle ranging from approximately 80° to 90° so that the center of tube lumens 54 at distal ends 53c are spaced from the distal end of probe 23 a distance of approximately 0.625 inch.

Tube distal ends 53c are joined by any suitable means such as soldering to a generally triangular-shaped plate 62 made from stainless steel or any other suitable material. Plate 62 has first and second generally planar surfaces 66 and 67 spaced apart a distance of approximately 0.07 inch. Spaced-apart first and second holes 68 and 69 extend through surfaces 66 and 67 for receiving tube distal ends 53c of first and second guide members 51 and 52. In this manner, each of plate holes 68 and 69 is in communication with a respective tube lumen 54. Plate 62 tapers inwardly toward longitudinal axis 24 as it extends distally from holes 68 and 69 and is provided with a rounded distal portion or tip 71.

Bridge assembly 22 of transurethral needle ablation device 21 further includes at least one irrigation tube and more specifically first and second irrigation tubes 76 and 77 carried by probe 23 and extending longitudinally within second side portion 26b of the probe 26 in a side by side manner (see FIGS. 1–7). Tubes 76 and 77 are each formed from an elongate tubular member 78 made from any suitable material such as stainless steel and having proximal and distal extremities 78a and 78b. Tube distal extremities 78b are slidably secured at probe distal extremity 23b by any suitable means such as solder 79 which further serves to provide a fluid-tight seal of probe second side bore portion 26b between guide members 76 and 77 and probe distal extremity 23b (see FIG. 5).

Each tubular member 78 has a circumferentially extending wall 81, shown particularly in FIG. 4, forming an internal lumen 82 which extends between proximal and distal extremities 78a and 78b and is formed with a rounded closed end 83 at the distal extremity 78b. An opening 86 extends through wall 81 adjacent closed end 83 and is in communication with lumen 82 (see FIG. 7). A deflection surface 87 extends opposite opening 86 and is preferably planar and aligned at an obtuse angle relative to the longitudinal axis of the tubular member. Proximal extremities 78a of tubular members 78 extend from the proximal extremity of probe 23 into internal chamber 46 where they curve approximately 90° relative to longitudinal axis 24 through an opening 91 in first half 31a of bridge 31.

First and second irrigation tubes 76 and 77 are slidably mounted in probe 23. In this regard, internal chamber 46 and opening 91 are cooperatively sized to receive a slide 92 through which proximal extremities 78a of the tubular members 78 extend (see FIGS. 1–3). First and second irrigation tubes 76 and 77 are longitudinally sized so that when slide 92 is in its first or proximal position in opening 91, as shown in solid lines in FIGS. 3, 6 and 7, the tubular members 78 are likewise in first or proximal positions with distal extremities 78b adjacent and beyond distal opening 28 of probe 23. Slide 92 and irrigation tubes 76 and 77 are movable to a second position, as shown in dashed lines in FIGS. 3, 6 and 7, in which the juxtaposed closed ends 83 of tubes 76 and 77 extend beneath plate 62 between and slightly beyond distal ends 53c of first and second guide members 51 and 52. When in this second position, the distal extremities of first and second irrigation tubes 76 and 77 extend across space 93 defined by the distal end of probe 23 and the distal extremities 53b of first and second guide members 51 and 52. Slide 92 serves as means for moving tubes 53 between these first and second positions. Means in the form of fittings 94 are secured to the proximal ends of first and second irrigation tubes 76 and 77 and permit a solution to be supplied to or withdrawn from the irrigation tubes.

At least one stand alone needle electrode assembly and, as shown more specifically in FIGS. 1 and 2, first and second needle electrode assemblies 101 and 102 are included within transurethral needle ablation device 21 for removable mounting to bridge assembly 22. Each of first and second electrode assemblies 101 and 102 includes an elongate cylindrical body 103 extending along a central longitudinal axis 104 and having proximal and distal extremities 103a and 103b (see FIGS. 8–10). Each cylindrical body 103 has a length and width so that it can be grasped and held by a human hand and, more specifically, has a length of approximately 3 inches and a width of approximately 0.5 inch. Each cylindrical body 103 includes a first cylindrical or tubular portion in the form of electrode control slide 106 and a second cylindrical or tubular portion in the form of insulation control slide 107.

Electrode control slide 106 is circular in cross-section and at least a portion thereof is concentrically carried within insulation control slide 107 so that control slides 106 and 107 are slidable relative to each other along axis 104 of body 103. The electrode control slide 106 is made from any suitable material such as polycarbonate and has a length of approximately 2 inches. Slide 106 is formed with a distal portion 108 having an external diameter of approximately 0.5 inch and a proximal portion 107 having a reduced diameter of approximately 0.375 inch. An axially extending central bore 111 extends from a closed proximal end of portion 107 to an opening 112 provided at the distal end of portion 108.

Insulation control slide 107 is made from any suitable material such as polycarbonate and has a length of approximately 1.75 inches. Slide 107 is circular in cross-section and is provided with a tubular distal portion 116 having an outer diameter approximately equal to the outer diameter of distal portion 108 of electrode control slide 106 and is provided with an axially-extending central bore 117 for slidably receiving proximal portion 109 of electrode control slide 106. Electrode control slide 107 further includes a proximal portion in the form of enlarged end cap 118.

A styler assembly or styler 121 is mounted in distal extremity 103b of cylindrical body 103 and includes a flexible radio frequency electrode 122 made from a superelastic shape memory alloy such as Nitinol or any other flexible conductive metal. Needle electrode 122 has an outer diameter of approximately 0.018 inch and has a proximal extremity 122a and a distal extremity 122b with a sharpened distal tip 123. Means is carried by electrode control slide 106 for mounting proximal extremity 122a of the needle electrode 122 to the electrode control slide and includes an adjustment screw 126 made from any suitable material such as stainless steel and threadedly carried within an axially-extending threaded bore 127 extending through the closed proximal end of insulation control slide proximal portion 109. Adjustment screw 126 has a bore 128 extending longitudinally therethrough for receiving proximal extremity 122a of needle electrode 122 and is formed with a distal extension 131 of reduced diameter which is crimped to secure the proximal extremity 122a of the needle electrode to adjustment screw 126.

Electrical conductor means is carried by cylindrical body 103 for permitting radio frequency energy to be supplied to needle electrode 122 and includes a cable 132 extending through a bore 133 in end cap 118 and having an internal wire 134 electrically coupled by any suitable means such as solder 136 to needle electrode proximal extremity 122a at adjustment screw 126. Cable 132 has a suitable connector 137 at its free end which permits electrical connection of needle electrode 122 to a suitable radio frequency generator (not shown).

Insulation means is included with each first and second electrode assembly 101 and 102 for encasing at least the proximal extremity 122a and exposing a preselected length of the distal extremity 122b of the respective needle electrode 122. More specifically, the insulation means includes an insulating sleeve 141 which is made from any suitable nonconductive material such as Nylon 11 insulation tubing having an outer diameter ranging from approximately 0.043 to 0.045 inch. Sleeve 141 is coaxially mounted on needle electrode 122 for longitudinal movement relative thereto.

Insulating sleeve 141 has a proximal end portion or extremity 141a and a distal end portion or extremity 141b with a tapered distal end.

Insulation control slide 107 includes means for securing proximal extremity 141a of the insulating sleeve 141 to the control slide 107 in a manner which permits longitudinal movement of the insulating sleeve relative to needle electrode 122. This securing means includes a tubular element 142 made from polycarbonate or any other suitable material which is circular in cross-section and is slidably carried within bore 111 of electrode control slide 106. Means which includes diametrically aligned first and second pins 143 is provided for rigidly securing tubular element 142 to insulation control slide 107 so that the tubular element moves longitudinally with the insulation control slide relative to electrode control slide 106. The electrode control slide 106 is provided with longitudinally-extending first and second longitudinally aligned and diametrically opposed slots 146 extending through the proximal portion 109 of the electrode control slide. Pins 143 extend radially inwardly through respective slots 146 and are secured at their outer ends by any suitable means such as being press fit into bores 147 extending radially through distal portion 116 of insulation control slide 107 and at their inner ends by any suitable means such as being press fit into diametrically aligned bores 148 extending into tubular element 142.

Tubular element 142 is provided with an axially-aligned central bore 151 extending therethrough for receiving proximal extremity 141a of insulating sleeve 141. At least the proximal portion of axial bore 151 is threaded so as to threadedly receive a set screw 152 provided with a central bore 153 extending along central axis 104 of cylindrical body 103. An elongate substantially rigid tubular member or tube 156 made from any suitable material such as 22.5 GA Hypotube has a proximal end 156a secured within bore 153 of the set screw 152 by any suitable means such as soldering. Tube 156 has an inside diameter of approximately 0.020 inch which is sufficient to slidably receive needle electrode 122 therein and has an outer diameter of approximately 0.025 inch. Tube 156 is received within a longitudinally-extending first lumen or bore 157 provided in insulating sleeve 141 and the insulating sleeve is heat shrunk about tube 156 so as to secure the insulating sleeve to tube 156 and thus to insulation control slide 107. As thus secured by tube 156 to tubular element 142, insulating sleeve 141 extends distally from tubular element 142. Tube 156, as so slidably carried about needle electrode 122, extends longitudinally along a significant portion of the needle electrode 122 and the insulating sleeve 141 and, more particularly, distal end 156b of tube 156 terminates a distance of approximately one inch from the distal end of the insulating sleeve.

When an electrode assembly 101 or 102 is in its first or contracted condition, as illustrated in solid lines in FIG. 8, distal portion 116 of the insulation control slide 107 generally abuts distal portion 106 of the electrode control slide 106 and tapered distal extremity 141b of insulating sleeve 141 extends to sharpened distal tip 123 of needle electrode 122 to expose a preselected length of approximately 0.04 to 0.05 millimeters of the needle electrode. Stylet 121 thus has a sharpened distal end with a substantially continuous taper. Cylindrical body 103 is movable to a second condition, illustrated in dashed lines in FIG. 8, by moving insulation control slide 107 proximally relative to electrode control slide 106. This extension of the cylindrical body is limited by the travel of pins 143 in longitudinally-extending slots 146. When a cylindrical body 103 is in its second or extended condition, insulating sleeve 141 is in its fully contracted condition to expose a preselected portion of the distal extremity 122b of the needle electrode. The amount by which electrode distal extremity 122b extends beyond insulating sleeve distal extremity 141b can be adjusted by rotating electrode adjustment screw 126 inwardly or outwardly relative to the threaded bore 127 provided within proximal portion 109 of the electrode control slide 106. As can be seen, control slides 106 and 107 are included within the means of each cylindrical body 103 for causing relative movement of the insulating sleeve 141 and the needle electrode 122 by moving the slides either toward or away from each other.

Temperature sensing means in the form of temperature sensor 161 is carried by distal extremity 141b of insulating sleeve 141 as illustrated in FIG. 8. A longitudinally-extending second lumen 162 is provided in the insulating sleeve and lead means in the form of first and second electrical leads 163 extend through second lumen 162 from proximal extremity 141a to distal extremity 141b where they electrically connect to temperature sensor 161 disposed within second lumen 162 adjacent the distal end of insulating sleeve 141 (see FIGS. 8 and 10). Set screw 152 is provided with a slot 166, shown in FIG. 9, extending longitudinally therethrough between its outer threads and its inner bore 153. Electrical leads 163 extend proximally from insulating sleeve proximal extremity 141a through slot 166 and a longitudinally-extending axially-offset second lumen or bore 167 provided in proximal portion 109 of electrode control slide 106 before extending into wire 133 and exiting removable end cap 118 through bore 133 therein.

First and second couplers 36 and 37 are included within the means of device 21 for mounting first and second electrode assemblies 101 and 102 to the device. Sleeves 38 of the first and second couplers 36 and 37 and cylindrical bodies 103 of first and second electrode assemblies 101 and 102 are respectively dimensioned so that the cylindrical bodies can be slidably received within sleeves 38 and stylers 121 slidably received within first and second guide members 51 and 52 when mounting the electrode assemblies to bridge assembly 22.

Cooperative means in the form of guide and locking assembly 171 is carried by each coupler 36 and 37 and respective electrode assembly 101 and 102 for securing the related cylindrical body 103 to the related sleeve 38. Assembly 171 includes a groove or slot 172 formed by opposed inner walls 173 in each sleeve 38 (see FIG. 1). Each slot 172 includes a first longitudinally-extending or longitudinal portion 172a, a first circumferentially-extending or circumferential portion 172b having a first end extending from the distal end of first portion 172a, a second longitudinal portion 172c extending distally from the second end of portion 172b and a second circumferential portion 172d extending from the distal end of portion 172c in the same direction as first circumferential portion 172b. Cylindrical body 103 is provided with a radially extending pin element or pin 176 press fit or otherwise suitably secured within a bore 177 extending into the circumferential wall of distal portion 108 of electrode control slide 106.

Pin 176 is sized to be cooperatively received within slot 172 of guide and locking assembly 171. As shown in FIG. 1, slot-forming inner wall 173 includes a first wall portion 173a which is included within the means of assembly 171 for restricting advancement of pin 177 in first longitudinal portion 172a of slot 172 and a second wall portion 173b which is included within the means of assembly 171 for restricting advancement of pin 176 within second longitudinal portion 172c of the slot. Inner wall 173 further includes a third wall portion 173c which is included within the means of assembly 171 for restricting proximal movement of pin 176 in slot 172 when the pin is disposed within second circumferential portion 172d of the slot.

Transurethral needle ablation device 21 is adapted for use with a conventional cystoscope such as cystoscope 181 shown in FIGS. 1–7. Cystoscope 181 is typically of a reusable type and is provided with a cylindrical stainless steel optical tube 182 which is adapted to fit with a slip fit within bridge 31 and probe 23. Optical tube 182 is well known to those skilled in the art and contains a plurality of rod-like optical elements collectively referred to herein and generally shown in FIG. 4 as optical element 183 to provide excellent viewing capabilities from oblique viewing surface or face 184 provided at distal extremity 182b of the optical tube. A fitting 187 is provided on the proximal extremity of optical tube 182 and carries a port 188 which can be connected to a light guide tube (not shown) connected into a conventional light source (not shown). An eyepiece 191 is carried by the fitting 187.

Means in the form of removable adapter 32 is carried by probe proximal extremity 23a for mounting cystoscope 181 to the proximal extremity of probe 23. The scope tube 182 is sized so that it can readily fit through central bore 48 of adapter 32 and scope guide tube 47 extending through central portion 26c of probe 23 between guide members 51 and 52 and irrigation tubes 76 and 77. A first O-ring 193 is mounted on the forward or distal end of adapter 32 to provide a fluid sealing fit between the adapter and bridge 31. A second O-ring 194 is carried by the adapter within adapter bore 48 proximal of scope guide tube 47. O-ring 194 engages scope optical tube 182 and serves to provide a fluid tight seal between tube 182 and the adapter so as to prevent fluid from leaking out the adapter bore 48. Conventional cooperative mating means (not shown) is carried by adapter 32 and fitting 187 for angularly locking the cystoscope with respect to the adapter and includes a longitudinally-extending recess in the adapter for receiving a longitudinally-extending projection or pin extending distally from scope fitting 187.

Operation and use of transurethral needle ablation device 21 in conjunction with performing a procedure on a human male patient is described in detail in copending U.S. patent application Ser. No. 08/191,258 filed Feb. 2, 1994. The procedure can briefly be described as follows. The anatomy of interest in the male patient to undergo the procedure consists of a bladder which is provided with a base or bladder neck which empties into a urethra extending along a longitudinal axis. The urethra can be characterized as being comprised of two portions: a prostatic portion and a penile portion. The prostatic portion is surrounded by a prostate or prostate gland which is a glandular and fibromuscular organ lying immediately below the bladder. The penile portion of the urethra extends through the length of a penis. The urethra is provided with a urethral wall which extends through the length of the penis and through the prostate into the bladder. The prostate can be characterized as being comprised of five lobes: interior, posterior, median, right lateral and left lateral. The prostate is also provided with a verumontanum.

Once the patient has been prepared, a conventional indifferent or grounding electrode is placed on the patient's backside so that it is adherent thereto and makes good electrical contact with the skin of the patient. The electrode is connected by an electrical cable into a control console and radio frequency generator (not shown). A conventional foot operated switch (not shown) can be connected by a cable into the console for controlling the application of radio frequency power.

Device 21 is prepared for the procedure by mounting first and second electrode assemblies 101 and 102 to first and second couplers 36 and 37 of the device while the electrode assemblies are in their respective first or contracted conditions. Cylindrical body 103 of the electrode assembly being mounted is grasped by the hand of the operating physician and the distal extremity of styler 121 inserted into sleeve 38 and then proximal extremity 53a of the respective guide member 51 or 52. Styler 121 is pushed through tube 53 of the guide member along the length thereof by the advancement of cylindrical body 103 toward sleeve 38. The initial loading of styler 121 into the coupler 36 or 37 and the advancement of the stylet distally through tube 53 is facilitated by substantially rigid support tube 156 disposed between the needle electrode 122 and insulating sleeve 141 of the styler 121. Tube 156 provides sufficient strength to the stylet so that it is not bent under its own weight during handling or while being pushed through the guide tube 53. The introduction of styler 121 into guide tube 53 is facilitated by the conical surface 57 at the distal end of central bore 41 which guides the end of the styler toward the center of bore 41 and into tube 53. The advancement of the stylet 121 through tube 53 is made easier by the continuous and smooth inner surface of the single integral tube 53 extending from central bore 41 to distal extremity 23b of probe 23.

Assembly 171 serves to guide and position the cylindrical body 103 within sleeve 38 and the stylet 121 within guide tube 53. As the cylindrical body 103 is advanced toward sleeve 38, pin 176 thereof is aligned with first longitudinal portion 172a of slot 172. Further advancement of the cylindrical body 103 relative to sleeve 38 in the direction of arrow 196 in FIG. 1 causes pin 176 to travel down first longitudinal portion 172a of slot 172 until the pin abuts first wall portion 173a at first circumferential portion 172b as illustrated in solid lines in FIG. 1 with respect to second electrode assembly 102. When the electrode assembly is so mounted to bridge 31, the styler thereof is carried within the respective guide tube 53 as illustrated in FIG. 4 where the styler is generally shown and identified by reference numeral 121. The first longitudinal portion 172a and needle electrode 122 are longitudinally sized so that distal extremity 122b of the needle electrode remains disposed within distal end 53c of guide tube 53 adjacent the respective hole 68 or 69 in plate 62 when pin 176 has engaged first wall portion 173a of sleeve 38. As such, no portion of the sharpened distal extremity 122b of needle electrode 122 is protruding from guide plate 62. Support tube 156, as discussed above, does not extend to the distal end of insulating sleeve 141 and thus permits the flexible distal end portion of stylet 121 extending beyond the support tube 156 to bend through the curved distal end 53c of guide tube 53.

Cystoscope 181 is mounted to bridge 31 by extending optical tube 182 through adaptor bore 48 into scope guide tube 47 extending along central portion 26c of probe 23. O-ring 194 provides a fluid tight seal between the optical tube 182 and the adapter. Optical tube 182 and probe 23 are relatively sized so that the cooperative engagement of scope fitting 187 with adapter 32 provides that distal extremity 182b of the optical tube is disposed within probe 23 adjacent distal extremity 23b of the probe. Relative angular rotation between cystoscope 181 and bridge 31 is restricted when fitting 187 and adapter 32 are cooperatively engaged so that the field of view of optical element 183 extends from oblique viewing face 184 forwardly of probe 23 toward guide plate 62. A suitable light source (not shown) is connected to port 188 to facilitate viewing with cystoscope 181 during the procedure.

Figure 7:
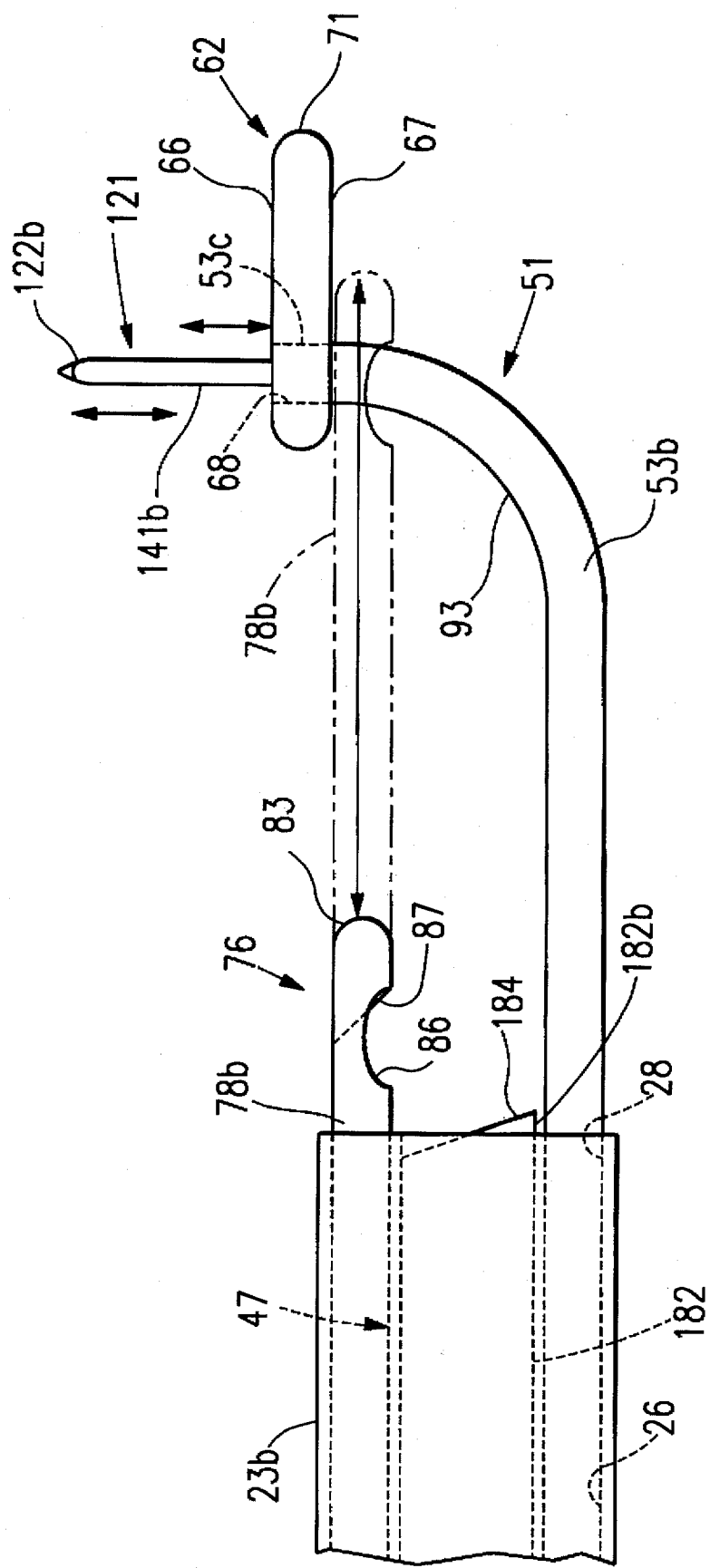
FIG. 7 is an enlarged view of the medical probe device of FIG. 1 taken along the line 7—7 of FIG. 3.

Slide 92 is pushed distally so that distal extremity 78b of each first and second irrigation tubes 76 and 77 extends across space 93 as shown in dashed lines in FIGS. 3, 6 and 7. This distal disposition of tubes 76 and 77 inhibits the urethral wall or other body tissue from being caught between guide plate 62 and distal extremity 23b of probe 23 as the probe is moved through the urethra. The outlet tube from a suitable pressurized saline solution or other flushing fluid supply source is connected to fittings 94 so as to provide a flow of the flushing fluid through device 21 during the procedure. After connector 137 has been electrically connected to a RF generator and control console for permitting the supply of radio frequency energy to needle electrodes 122 and the monitoring of the temperature at temperature sensors 161, transurethral needle ablation device 21 is ready for use.

Probe distal extremity 23b of device 21 is introduced into the urethra with both electrode assemblies 101 and 102 mounted to bridge 31 in the position shown in FIG. 1 with respect to second electrode assembly 102. The distal extremity 23b is advanced through the urethra until in the vicinity of the prostate. During advancement, blunt end tip 71 of plate 62 guides the device through the urethra. A steady flow of flushing fluid into the urethra via first and second irrigation tubes 76 and 77 facilitates viewing the urethral wall with cystoscope 181 so that the operating physician can ascertain when guide plate 62 is in the desired registration with the prostate. First wall portions 173a protect against premature advancement of needle electrodes 122 during disposition of the probe in the urethra. Probe 23 has a length, as discussed above, which is sufficient to permit probe distal extremity 23b to be in the vicinity of the prostate when probe proximal extremity 23a is outside of the urethra.

Device 21 is free of obstructions which may inhibit the operating physician from continually viewing the urethra while advancing and/or rotating device 21 during the procedure. In this regard, the sidewise disposition of first and second couplers 36 and 37 move first and second electrode assemblies 101 and 102 and related wires 133 away from eyepiece 191. The couplers and electrode assemblies are longitudinally sized so that insulation control slides 107 do not contact the physician's face while in either their proximal position, as shown in solid lines in FIG. 1 with respect to second electrode assembly 102, or in their distal position, as shown in solid lines in FIG. 1 with respect to first electrode assembly 101.

After probe 23 has been properly positioned in the urethra of the patient, the operating physician pulls on slide 92 to cause first and second irrigation tubes 76 and 77 to retract proximally into probe 23 to their proximal positions shown in solid lines in FIGS. 3, 6 and 7. The operating physician can now better observe through cystoscope 181 the deployment of stylets 121 through guide plate 62 sidewise of longitudinal axis 24 as the space 93 between optical viewing face 184 and guide plate 62 is now generally unobstructed. Flushing fluid can be introduced through irrigation tubes 76 and 77 to increase visibility within space 93 and, in this regard, openings 86 and deflection surfaces 87 in the guide tubes 78 are included within the means of device 21 for directing the flushing fluid toward and against the viewing face 184 of cystoscope 181.

In a typical procedure, the operating physician grasps and positions device 21 with one hand so that planar bridge 31 is generally vertically disposed. One electrode assembly is positioned near the forehead of the operating physician and the other electrode assembly is positioned near the chin of the operating physician. With the device 21 so positioned, the distal extremities of guide members 51 and 52 are aligned so as to introduce stylers 121 into the prostate.

The operating physician now uses his or her other hand to sequentially advance stylers 121 of first and second electrode assemblies 101 and 102 into the portion of the prostate to be treated. For example, if device 21 is positioned so that plate holes 68 and 69 open to the left of the operating physician, the physician may first reach to first electrode assembly 101 near his or her forehead and grasp end cap 118 thereof. The operating physician unlocks the styler 121 of assembly 101 for advancement by rotating the end cap 118 in a counterclockwise direction. This rotational motion is transmitted to the electrode control slide 106 by the engagement of pins 143 with the sidewalls of slots 146 so that pin 176 carried by the electrode control slide travels through first circumferential portion 172b of slot 172 until it is in longitudinal alignment with second longitudinal portion 172c. Thereafter, the operating physician pushes cylindrical body 103 further into sleeve 38 in the direction of arrow 197 in FIG. 1 until pin 176 engages second wall portion 173b of sleeve 38 and is precluded from further advancement relative to the sleeve. The sharpened distal extremity 122b of needle electrode 122 followed by the insulating sleeve 141 pierce the urethral wall during such advancement of the styler 121.

Second longitudinal slot portion 172c and stylet 121 are each longitudinally sized so that sharpened distal extremity 122b of needle electrode 122 has advanced a predetermined amount ranging from 14 to 22 millimeters from guide plate hole 68 when pin 176 engages wall portion 173b. As can be appreciated, the amount of this extension is dependent upon the size of the prostate being ablated. Accordingly, electrode assemblies 101 and 102 can be provided with needle electrodes 122 of varying lengths to accommodate these different sized prostates and be within the scope of the present invention.

Distal extremity 141b of insulating sleeve 141 is retracted relative to needle electrode 122 so as to expose a greater portion the needle electrode extending from guide tube 53. The operating physician retracts insulating sleeve 141 after rotating cylindrical body 103 in the counterclockwise direction so that pin 176 travels into second circumferential portion 172d of slot 172 as shown in FIG. 1 with respect to pin 176 of first electrode assembly 101. Opposed inner wall portions 173b and 173c forming slot portion 172d serve to longitudinally trap pin 176 and preclude electrode control slide 106 and needle electrode 122 carried thereby from advancing or withdrawing relative to guide plate 62. The operating physician then pulls on end cap 118 in the direction of arrows 198 in FIG. 1 to move insulation control slide 107 and tubular element 142 secured thereto proximally relative to electrode control slide 106. The insulation control slide 107 of first electrode assembly 101 is illustrated in dashed lines in FIG. 1 in such a proximal position. As can be appreciated, third wall portion 173c facilitates this relative movement between control slides 107 and 106 by precluding electrode control slide 106 from moving proximally with the insulation control slide.

The retraction of insulating sleeve 141 relative to needle electrode 122 minimizes undesirable tenting in the urethral wall due to introduction of styler 121 into the prostate. In this regard, slots 146 in electrode control slides 106 are longitudinally sized so that the distal end of insulating sleeve 141 retracts to a distance ranging from 5 to 7 millimeters from guide plate 62 when insulation control slide 106 is in its proximal most position relative to the electrode control slide 107. As can be appreciated, the length of slots 146 is longer for needle electrodes for use in larger prostates and smaller for needle electrodes for use in smaller prostates.

The operating physician deploys stylet 121 of second electrode assembly 102 by moving his or her hand from assembly 101 to the end cap 118 of assembly 102. The styler of assembly 102 is advanced into the prostate and insulating sleeve 141 thereof retracted in the same manner as described above for electrode assembly 101.

Radio frequency energy is supplied to needle electrodes 122 in the manner set forth in copending U.S. patent application Ser. No. 08/191,258 filed Feb. 2, 1994 to create lesions in the target volumes of prostatic tissue in the vicinity of the exposed portions of the needle electrodes. These lesions serve to shrink the size of the prostate. During the needle ablation procedure, temperature sensors 161 permit the temperature of the tissue being ablated to be measured. The portion of insulating sleeves 141 extending beyond guide plates 62 protect the urethral wall from being ablated during the application of radio frequency energy to needle electrodes 121.

Once the needle ablation has been completed in these portions of the prostate, needle electrodes 122 are withdrawn from the prostate. For each needle electrode, the operating physician rotates the related end cap 118 in a clockwise direction to cause pin 176 to travel back through second circumferential slot portion 172d to second longitudinal slot portion 172c. Longitudinal movement of electrode control slide 106 relative to the sleeve 38 is now permitted. The operating physician retracts the distal extremity of styler 121 back into guide tube 53 by pulling on end cap 118 to cause pin 176 to travel proximally through the second longitudinal slot portion 172c to first circumferential slot portion 172b.

In a typical procedure, further ablations are performed in other target volumes or areas within the prostate. Preparatory to these further ablations, each stylet 121 is reloaded for deployment by rotating the respective end cap 118 clockwise so that pin 176 travels into the first circumferential slot portion 172b. With pin 176 now precluded from distal longitudinal movement in slot 172 by first wall portion 173a, the operating physician causes insulating sleeve distal extremity 141b to extend fully along needle electrode distal extremity 122b by pushing on end cap 118 until pins 143 travel to the distal end of respective slots 146 in the electrode control slide 106. Device 21 is then rotated approximately 180° within the urethra so that plate holes 68 and 69 are directed to other portions of the prostate to be treated. The stylets of first and second electrode assemblies are then advanced and positioned in the prostate in the same manner as discussed above and radio frequency energy supplied thereto.

After completion of the last ablation procedure, stylers 121 are removed from the prostate in the manner discussed above and device 21 is withdrawn from the urethra. Irrigation tubes 76 and 77 can be moved to their distal disposition during removal of device 21 from the urethra.

Upon completion of the procedure, first and second electrode assemblies 101 and 102 are easily removed from bridge 31. Cystoscope 181 is removed from the bridge and cleaned and sterilized for use in another procedure. Bridge assembly 22 can also be reused in another procedure after it has been flushed and sterilized. The open construction and composition of the bridge assembly facilitate its flushing and sterilization. Sterilization fluids can be easily introduced through adaptor bore 48 and scope guide tube 47 and through both the proximal and distal extremities 53a and 53b of guide tubes 53 and the proximal and distal extremities 78a and 78b of tubular members 78. If desired and/or necessary during sterilization, bridge halves 31a and 31b can be disassembled so that the bridge 31 can be separated from probe 23. In addition, first and second irrigation tubes 76 and 77 can be slidably removed from probe 23 and adapter 32 removed from the bridge. As can be appreciated by those skilled in the art, the ease in which bridge 31 can be sterilized permits its reuse in subsequent procedures so as to reduce the overall per patient cost of the transurethral needle ablation procedure herein described.

Although first and second tubes 76 and 77 have been referred to and discussed herein as irrigation tubes, it should be appreciated that one or both of these tubes could be utilized for aspiration and be within the scope of the present invention. Any such aspiration could be simultaneous with or sequential to supply of the flushing fluid through device 21.

It can also be appreciated that removable adapter 32 permits its replacement with similar adapters configured for use with other conventional rod lens cystoscopes. Accordingly, device 21 can be used with a plurality of conventional rod lens cystoscopes. In addition, device 21 can be used with a fiber-optic type cystoscope and be within the scope of the present invention. Further, although device 21 described above includes a removable scope adapter 32, it should be appreciated that a device similar to device 21 could be provided with a nonremovable adapter which is formed integral with or fixedly secured to bridge 31 and is configured to mate only with a single scope or certain scopes.

In another embodiment of the transurethral needle ablation device of the present invention, an electrode assembly can be provided in which the insulation means consists of an insulating coating encasing at least a portion of one or both needle electrodes 122. The coating would terminate short of the distal end of the needle electrode so as to expose a predetermined amount of the needle electrode. Such an insulating coating would not permit relative longitudinal movement between the insulation means and the needle electrode during the procedure. However, as can be appreciated, a variety of electrode assemblies having electrodes and insulating coatings of differing sizes could be provided.

Further, a medical probe device can be provided in which first and second irrigation tubes 76 and 77 are fixedly secured within probe 23 so that openings 86 therein are always adjacent to the distal opening of probe 23 for permitting the viewing of needle electrodes being advanced from guide plate 62.

Embodiments of the transurethral needle ablation device of the present invention can also be provided in which the needle electrodes advance from guide plate 62 at an angle other than 90°. Such an embodiment is illustrated in FIGS. 11–14 where a transurethral needle ablation device 206 is illustrated. Device 206 is substantially similar to device 21 and like components have been identified by like reference numbers.

Bridge assembly 207 of device 206 includes handle means which is mounted on proximal extremity 23a of probe 23 and has a bridge 208 substantially similar to bridge 31. Bridge 208 has halves 208a and 208b and a proximal extremity in the form of removable adapter 211 which is substantially similar to adapter 32 of device 21. Bridge further includes oppositely aligned first and second coupling means or couplers 36 and 37 not shown in FIGS. 1–14. Bridge halves 208a and 208b are provided with respective cavities therein which form an internal chamber 212 within bridge 208. Chamber 212 is in communication with bore 26 in probe 23 and a bore 213 extending through adapter 211 along longitudinal axis 24 of device 206. Unlike device 21 described above, device 206 does not include a guide tube extending from adapter 211 through internal chamber 212 and probe 23 similar to scope guide tube 47 of device 21.

First and second guide members 216 and 217, substantially similar to first and second guide members 51 and 52 of device 21, extend respectively from first and second couplers 36 and 37 through internal chamber 212 and first side bore portion 26a of probe 23 to probe distal extremity 23b. Guide members 216 and 217 each include a single tube 218 which is substantially similar to tube 53 of device 21 and has a distal extremity 218b and a distal end 218c. Each tube 218 is provided with an internal lumen 221. Tube distal extremities 218b are secured to the inside of probe wall 27 adjacent distal opening 28 by solder 219 and thereafter diverge with respect to longitudinal axis 24 as they extend distally out of probe bore 26 at an angle ranging from approximately 20° to 30° so as to form a space therebetween substantially similar to space 61 of device 21. The diverging tube distal extremities simultaneously curve alongside longitudinal axis 24 through an angle of approximately 10° (see FIGS. 11 and 14). Tube distal ends 218c extend through respective first and second holes 68 in 69 and guide plate 62 and are secured therein by any suitable means such as soldering. In this manner, each of plate holes 68 and 69 is in communication with a respective tube lumen 221.

Device 206 is adapted for use with a conventional cystoscope such as cystoscope 181 described above. A first O-ring 222 is carried by the forward or distal end of adapter 211 to provide a fluid sealing fit between the adapter and bridge 208. A second O-ring 223 is carried by the adapter within adapter bore 213 for engaging scope optical tube 182 and thus providing a fluid tight seal between tube 182 and the adapter.

Device 26 includes means in the form of irrigation assembly 226 for introducing a flushing fluid into and/or aspirating a flushing fluid from probe distal extremity 23b. Bridge 208 is formed with a port 227 provided with an opening 228 in communication with internal chamber 212. A removable plug 231 made from any suitable material such as polycarbonate is sized and shaped to sealably secure to port 227 at opening 228 and carries first and second tubes 232 having internal lumens 233 in communication with respective bores 236 extending through plug 231 into opening 228. Each tube 232 carries a valve 237 for regulating or restricting flow through its lumen 233. Means in the form of fittings 238 are secured to the free ends of tubes 232 for permitting a solution to be supplied to or withdrawn from the tubes.

Means is carried by probe distal extremity 23b for directing the flow of flushing fluid passing through second side bore portion 26b against viewing face 184 of cystoscope 181 and includes a fluid guide or baffle 243 made from any suitable material such as stainless steel and having the general shape of an arrowhead. The elongate baffle 243 has proximal and distal end portions 243a and 243b and an outer surface 244 which, as illustrated in cross section in FIG. 12, conforms to the inner shape of probe wall 27. Baffle 243 is secured to the inside of probe wall 27 at probe distal opening 28 by any suitable means such as solder so that proximal end portion 243a extends into probe second side bore portion 26b as illustrated in FIGS. 13 and 14. The baffle has a conformation which tapers as it extends toward proximal end portion 243 to minimize the resistance created thereby to the flushing fluid passing through probe bore 26 toward distal end portion 243b of the baffle. In this regard, baffle 243 has an inner surface 246 with an inclined proximal portion 246a. Distal end portion 243b of baffle 243 is rounded.

At least one and as illustrated in FIGS. 12 and 13 first and second longitudinally-extending fluid guide channels 247 are provided in inner surface 246 of baffle 243. Each fluid guide channel 247 extends through proximal end portion 243a and has a closed distal end in the form of deflection surface 248 as shown in FIGS. 13 and 14. Each of the fluid guide channels 247 is generally semi-circular in cross-section as shown in FIG. 12. Baffle 243 is mounted to probe distal extremity 23b so that fluid guide channels 247 extend distally beyond viewing face 194 of cystoscope 181.

At least one and as illustrated in FIGS. 13 and 14 first and second spaced-apart longitudinally-extending elongate members or rods 251 extend between baffle 243 and guide plate 62. Each of the rods 251 is made from any suitable material such as stainless steel and has a proximal end portion 251a soldered or otherwise suitably secured to one side of distal end portion 243b of the baffle 243 and a distal end portion 251b soldered or otherwise suitably secured to the related side of plate 62 at the proximal end of the plate. Rods 251 diverge from each other as they extend across space 93.

The operation and use of transurethral needle ablation device 206 is substantially similar to the operation described above with respect to device 21. Cystoscope 181 is mounted to bridge 208 by extending optical tube 182 through adapter bore 213 and internal chamber 212 into central portion 26c of probe bore 26. Optical tube 182 engages inclined surface portion 246a of baffle 243 as it approaches probe distal extremity 23 and the inclined surface portion 246a serves to center the optical tube within probe bore 26 and capture it between distal end portion 243b of the baffle and first and second guide members 216 and 217 extending along first side bore portion 26a of the probe (see FIGS. 12 and 14).

During the introduction of probe 23 into the urethra, a saline solution or other suitable flushing fluid can be introduced through first and second irrigation tubes 232. The flushing fluid travels through internal chamber 212 and probe bore 26 so as to flow out probe distal opening 28 around scope optical tube 182 and first and second guide members 216 and 217. Since second side bore portion 26b at probe distal opening 28 is relatively unobstructed, a significant portion of the flushing fluid is directed to baffle 243. First and second fluid guide channels 247 of the baffle serve to guide the flushing fluid to baffle deflection surface 48 which directs the fluid downwardly onto viewing face 184 of optical element 183. In this manner, the flow of flushing fluid through device 206 serves to enhance the visibility through cystoscope 181.

It should be appreciated that the flushing fluid can be introduced through one of tubes 232 and aspirated through the other tube 232. Valves 237 permit closure of the aspirating tube during introduction of the flushing fluid and likewise permit closure of the introduction tube during aspiration of the flushing fluid.

First and second rods 251 serve to inhibit the urethra wall or other tissue within the urethra from becoming caught between baffle 243 and guide plate 62 during the introduction of probe 23 into the urethra, but permit viewing distally of probe 23 and viewing of stylers 121 being advanced from guide plate 62.

During introduction of stylets 121 into the portion of the prostate to be treated, tube distal extremities 218b of first and second guide members 216 and 217 serve to direct the stylets 121 at an angle other than 90° relative to plate 62. As discussed above, first and second guide members 216 and 217 direct the distal extremities of stylets 121 at an angle of approximately 10° relative to guide plate 62. Such a deployment of stylets 121 facilitates treatment of the median lobe portion of the prostate.

The simplified structure of transurethral needle ablation device 206 relative to device 21 further facilitates sterilization and reuse of device 206. The absence of separate irrigation tubes similar to tubes 76 and 77 of device 21 and the absence of a scope guide tube similar to tube 47 of device 21 permits sterilization fluids to be easily flushed through probe 23 and bridge 208. Plug 231 and adapter 211 can be removed during the sterilization procedure.

It should be appreciated that a transurethral needle ablation device which incorporates various features of device 21 and device 206 would be within the scope of the present invention.

In view of the foregoing, it can be seen that a medical probe device has been provided which can be utilized for a transurethral needle ablation procedure in the prostate of a human male. The device includes a bridge assembly which can be easily sterilized for reuse and a removable stand alone electrode assembly which can be discarded after a single use. A plurality of electrode assemblies having different sized electrodes to fit large, medium and small prostates are provided. The device can be used with a plurality of conventional rod lens scopes and includes means for flushing the scope lens during the procedure.

What is claimed is:

1. A medical probe device for medical treatment of tissue of a patient's prostate through a wall of the patient's urethra, comprising:
   a) a probe shaft having proximal and distal extremities and a longitudinal axis,
   b) handle means mounted on the proximal extremity of the probe shaft for introducing the probe shaft into the patients urethra so that the distal extremity of the probe housing is in the vicinity of the patient's prostate,
   c) first and second guide tubes provided with interior chambers therein and having distal extremities, the first and second guide tubes extending distally of the probe housing and extending at an angle with respect to the longitudinal axis to form a space between the distal extremity of the probe housing and the distal extremities of the first and second guide tubes, and
   d) a plate having a rounded distal portion secured to the distal extremities of the first and second guide tubes, the plate having holes therein in communication with the lumens in the first and second guide tubes.

2. A medical probe device as in claim 1 wherein the distal extremities of the first and second guide tubes form a space therebetween.

3. A medical probe device as in claim 1 further comprising at least one elongate member extending across the space between the distal extremity of the probe housing and the plate for inhibiting tissue entering the space when the device is moved in the urethra.

4. A medical probe device as in claim 3 wherein the elongate member comprises an irrigation tube slidably mounted in the probe housing and movable across the space along the longitudinal axis.

5. A medical probe device as in claim 4 further comprising a fitting coupled to the probe housing for permitting a liquid to be supplied to the irrigation tube.

6. A medical probe device as in claim 1 adapted for use with a scope having an optical element with a field of view, further comprising means carried by the probe housing adapted for mounting the scope to the proximal extremity of the probe housing so that the optical element is positioned in the probe housing and the field of view extends forwardly of the probe housing.

7. A medical probe device as in claim 6 wherein the optical element has a distal viewing face, means carried by the distal extremity of the probe housing for directing a flow of flushing fluid against the distal viewing face.

8. A medical probe device as in claim 6 wherein said means permits the optical element of the scope to be positioned in the distal extremity of the probe housing so that the field of view permits viewing a flexible radio frequency electrode being advanced from the holes in the plate sidewise of the longitudinal axis.

9. A medical probe device for medical treatment of tissue of a patient's prostate through a wall of the patient's urethra wall comprising a probe housing having proximal and distal extremities and a longitudinal axis, handle means mounted on the proximal extremity of the probe housing for introducing the distal extremity of the probe housing into the urethra so that the distal extremity of the probe housing is in the vicinity of the prostate, at least one guide tube carried by the probe housing and having a distal extremity in the vicinity of the distal extremity of the probe housing, the guide tube being provided with a lumen therein and the handle means being provided with coupling means in communication with the lumen of the guide tube, at least one body having a length and width so that it can be grasped and held by a human hand, the body having proximal and distal extremities and a central axis, a radio frequency electrode having a proximal extremity mounted in the cylindrical body and a sharpened distal extremity, insulation sleeve coaxially mounted on the radio frequency electrode means carried by the handle means for causing relative movement between the insulating sleeve and the radio frequency electrode to expose a preselected length of the sharpened distal extremity of the radio frequency electrode, electrical conductor means carried by the cylindrical body and electrically coupled to the radio frequency electrode at one end and having an electrical connector at the other end for permitting radio frequency energy to be supplied to the radio frequency electrode, cooperative mating means carried by the coupling means and the body for securing the body to the handle means so that the radio frequency electrode is disposed in the guide tube and the preselected length of the sharpened distal extremity of the radio frequency electrode is in the vicinity of the distal extremity of the probe housing.

10. A medical probe device as in claim 9 wherein the guide tube consists of a single tube extending continuously from the coupling means to the distal extremity of the probe housing.

11. A medical probe device as in claim 9 wherein the body is circular in cross-section and includes first and second portions slidable relative to each other along the central axis of the body, the flexible radio frequency electrode being secured to the first portion and the insulating sleeve being secured to the second portion.

12. A medical probe device as in claim 11 wherein the coupling means includes a sleeve for slidably receiving the body and the cooperative mating means includes means for restricting advancement of the first portion of the body relative to the sleeve after the flexible radio frequency electrode has been advanced a preselected amount from the distal extremity of the guide tube.

13. A medical probe device as in claim 12 wherein the cooperative mating means includes means for restricting withdrawal of the first portion of the body relative to the sleeve so as to facilitate proximal movement of the second portion of the body relative to the sleeve and thus expose a greater amount of the flexible radio frequency electrode advanced from the distal extremity of the guide tube.

14. A medical probe device as in claim 13 wherein the first portion of the body includes a radially extending pin element and wherein the sleeve includes a slot formed by opposed inner walls for receiving the pin element, the opposed inner walls having a circumferentially-extending portion for restricting longitudinal advancement of the pin in the slot after the flexible radio frequency electrode has advanced within the guide tube to the distal extremity of the guide tube.

15. A medical probe device as in claim 14 wherein the opposed inner walls have an additional circumferentially-extending portion longitudinally-spaced apart from the first named circumferentially-extending portion for restricting longitudinal movement of the pin in the slot after the radio frequency electrode has advanced the preselected amount from the distal extremity of the guide tube.

16. A medical probe device as in claim 9 further comprising a second guide tube and coupling means of the same type as the first named guide tube and coupling means, wherein the body, the flexible radio frequency electrode, the insulation means and the electrical conductor means comprise a first electrode assembly, further comprising a second electrode assembly of the same type as the first electrode assembly and second cooperative mating means carried by the second coupling means and the second body for securing the second electrode assembly to the handle means in the same manner as the first electrode assembly is secured to the handle means by the first coupling means.

17. A medical probe device as in claim 16 wherein the handle means is generally planar and the first and second coupling means symmetrically secure the first and second electrode assemblies to the handle means so that the first and second bodies extend in the plane of the handle means.

18. A medical probe device as in claim 17 adapted for use with a scope having an optical element with a field of view, further comprising means carried by the handle means for mounting the scope to handle means so that the optical element is positioned in the probe housing and the field of view extends forwardly of the probe housing.

19. A medical probe device as in claim 18 wherein the optical element has a distal viewing face, means carried by the distal extremity of the probe housing for directing a flow of flushing fluid against the distal viewing face.

20. An elongated intracorporeal ablation device, comprising a) an elongated shaft having proximal and distal ends, at least one inner lumen which extends from the proximal end to the distal end of the shaft, a longitudinal axis and means on the distal end of the shaft for directing the inner lumen in the distal end of the shaft in a direction lateral to the longitudinal axis thereof;

b) a handle on the proximal end of the shaft having an interior chamber, a wall portion which defines at least in part the interior chamber;

c) an elongated cartridge assembly comprising
an elongated energy transmitting member which is a least in part configured to be slidably received within the inner lumen extending within the shaft of the ablation device and to extend out the distal end of the shaft, which has proximal and distal extremities and which has means to emit energy from the distal extremity toward tissue to be ablated,
an insulating jacket with proximal and distal ends surrounding at least a significant length of the elongated energy transmitting member, means to provide resistive movement between the insulating jacket and the elongated energy transmitting member to control the length of the distal extremity of the elongated energy transmitting member extending out the distal end of the insulating jacket, means to connect the proximal extremity of the energy transmitting member to a source of suitable energy, and a cartridge housing which is connected to the proximal extremity of the energy transmitting member and which is configured to be slidably disposed within the interior chamber of the handle of the ablation device; and d) means to move the cartridge assembly longitudinally within the ablation device.

21. The ablation device of claim 1 wherein the cartridge housing has a protrusion on the exterior thereof which is configured to extend out a slot provided in the handle to guide the movement of the cartridge housing within the handle.

22. The ablation device of claim 1 wherein the energy transmitting member is an electrical conducting member.

23. The ablation device of claim 22 wherein the electrical conducting member has a proximal end with an electrical connector.

24. The ablation device of claim 1 wherein the cartridge housing comprises a distal push tube which receives and secures the proximal extremity of the insulation jacket and a proximal control tube connected to the distal push tube whereby longitudinal movement of the proximal control tube effects longitudinal movement of the distal push tube.

25. The ablation device of claim 24 wherein the handle is provided with an longitudinally extending slot and wherein the proximal push tube and distal control tube are connected by a rod which extends through the longitudinally extending slot.

26. A medical probe device for treatment of a patient's prostate through a wall of the patient's urethra, comprising:

a) an elongated probe shaft having proximal and distal ends, an inner lumen extending between the proximal and distal ends and a longitudinal axis, b) a handle mounted on the proximal end of the probe shaft having an interior chamber in communication with the lumen in the elongated probe shaft and having a slot in a wall portion of the handle which defines at least in part the interior chamber which extends in a longitudinal direction;

c) an ablation cartridge assembly disposed at least in part within the inner chamber of the handle which comprises a first cartridge housing member having an interior chamber and a guiding member extending from an exterior portion of the first cartridge housing member configured to be slidably received within the slot in the wall of the handle;

a second cartridge housing member having an interior chamber in communication with the interior chamber of the first cartridge housing member and having at least a portion thereof slidably disposed within the interior chamber of the first cartridge housing member;

an elongated energy transmitting member having an energy receiving proximal end, an energy emitting distal end extending within the elongated shaft to a distal extremity thereof and a proximal extremity secured to the first housing member;

an insulating tubular jacket slidably disposed over the exterior of the elongated energy transmitting member having proximal and distal ends with a distal extremity secured to the second housing member, whereby relative axial movement between the first and second housing members effecting relative movement between the energy transmitting member and the insulating jacket to adjust the length of the energy transmitting member which extends out the distal end of the insulating jacket;

d) a rounded distal tip on the distal end of the elongated probe having means to guide the distal ends of the energy transmitting member and the insulating jacket in a curved pathway in a direction away from the longitudinal axis of the elongated probe to facilitate the advancement of the distal ends into the patient's prostate.

27. A method of treating a patient's prostate comprising:

a) providing a medical probe device which includes i. an elongated probe housing having proximal and distal extremities, an interior extending between the proximal and distal extremities and a longitudinal axis, ii. a handle mounted on the proximal extremity of the probe shaft having an inner chamber in communication with the lumen in the elongated probe housing and with a slot therein extending in a first direction and then in a second direction perpendicular to the first direction;

iii. an ablation assembly disposed at least in part within the inner chamber of the arm of the adapter which comprises a first housing member having an interior chamber and a guiding member extending from an exterior portion of the first housing member configured to be slidably received within the slot in the arm of the adapter;

a second housing member having an interior chamber and having at least a portion thereof slidably disposed within the interior chamber of the first housing member;

an elongated energy transmitting member disposed in part within the interior chambers of the first and second housing members having an energy receiving proximal end extending out of the second housing member, an energy emitting distal end extending within the elongated probe housing to a distal extremity thereof and a proximal extremity secured to the first housing member;

an insulating tubular jacket slidably disposed over the exterior of the elongated energy transmitting member having proximal and distal ends with a distal extremity secured to the second housing member, whereby relative axial movement between the first and second housing members effecting relative movement between the energy transmitting member and the insulating jacket to adjust the length of the energy transmitting member which extends out the distal end of the insulating jacket;

iv. a rounded distal tip on the distal end of the elongated probe having means to guide the distal ends of the energy transmitting member and the insulating jacket in a curved pathway in a direction away from the longitudinal axis of the elongated probe to facilitate the advancement of the distal ends into the patient's prostate;

b) introducing the medical device into the patient's urethra and advancing the medical device therein until the rounded distal tip on the distal end of the elongated probe is disposed within the patient's prostatic urethra;

c) advancing the ablation assembly distally within the arm of the adapter to advance the distal ends of the energy transmitting member and the insulating tube into the patient's prostate;

d) withdrawing the second housing member of the ablation assembly out of the second housing member to adjust the length of exposed energy transmitting member within the patient's prostate; and e) delivering energy through the energy transmitting member to the region of the patient's prostate surrounding the exposed portion of the energy transmitting member to ablate prostate tissue in said region.

* * * * *

UNITED STATES PATENT AND TRADEMARK OFFICE
CERTIFICATE OF CORRECTION

PATENT NO. : 5,681,276

DATED : October 28, 1997

INVENTOR(S) : Ingemar H. Lundquist

It is certified that error appears in the above-indentified patent and that said Letters Patent is hereby corrected as shown below:

On the cover page under "FOREIGN PATENT DOCUMENTS", the first patent should be changed from "9210142" to --WO92/10142--.

Column 5, line 28, change "A styler assembly or styler 121" to --A stylet assembly or stylet 121--.

Column 7, line 37, change "styler" to --stylet--.

Column 9, lines 8, 13, 17, 20, 22, 37 and 39, change "styler" to --stylet--.

Column 11, lines 2, 4, 10, 25, and 61, change "styler" to --stylet--.

Column 12, lines 5, and 29, change "styler" to --stylet--.

Column 12, line 51, change "stylers" to --stylets--.

Column 15, line 62, change "stylers" to --stylets--.

Column 9, line 10, change "Styler" to --Stylet--.

UNITED STATES PATENT AND TRADEMARK OFFICE
CERTIFICATE OF CORRECTION

PATENT NO. : 5,681,276

DATED : October 28, 1997

INVENTOR(S) : Ingemar H. Lundquist

It is certified that error appears in the above-identified patent and that said Letters Patent is hereby corrected as shown below:

Column 19, line 1, change "resistive" to --relative--.

Signed and Sealed this

Fifth Day of May, 1998

Attest:

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,681,276
DATED : October 28, 1997
INVENTOR(S) : Ingemar H. Lundquist It is certified that error appears in the above-indentified patent and that said Letters Patent is hereby corrected as shown below:

Column 18, line 58 after "which is" delete "a" and insert --at--.

Signed and Sealed this

First Day of June, 1999

Attest:

Q. TODD DICKINSON

Attesting Officer

Acting Commissioner of Patents and Trademarks